(12) United States Patent
Lehtonen

(10) Patent No.: US 6,261,829 B1
(45) Date of Patent: Jul. 17, 2001

(54) PROCESS FOR COMBATING MICROORGANISMS

(75) Inventor: Paavo Lehtonen, Kirkkonummi (FI)

(73) Assignee: Genencor International, Inc., Rochester, NY (US)

( * ) Notice: Subject to any disclaimer, the term of this patent is extended or adjusted under 35 U.S.C. 154(b) by 0 days.

(21) Appl. No.: 08/287,056

(22) Filed: Aug. 8, 1994

Related U.S. Application Data

(63) Continuation of application No. 07/852,129, filed on Jun. 15, 1992, now abandoned.

(30) Foreign Application Priority Data

Oct. 24, 1989 (WO) ................................. PCT/FI90/00251
Oct. 27, 1989 (FI) ...................................................... 895115

(51) Int. Cl.$^7$ ...................................................... C12S 5/00
(52) U.S. Cl. ...................... 435/264; 424/94.4; 435/262; 435/267; 435/266
(58) Field of Search .......................... 424/94.4; 435/192, 435/190, 262, 264, 266, 267, 800; 162/161, 190; 210/632, 764, 928

(56) References Cited

U.S. PATENT DOCUMENTS

| 2,482,724 | * | 9/1949 | Baker | 435/190 |
| 4,414,334 | * | 11/1983 | Hitzman | 435/190 |
| 4,478,683 | * | 10/1984 | Orndorff | 435/190 |
| 4,996,062 | | 2/1991 | Lehtonen | 426/8 |

FOREIGN PATENT DOCUMENTS

1468405 * 3/1977 (GB).

* cited by examiner

Primary Examiner—Jean C. Witz
(74) Attorney, Agent, or Firm—Genencor International, Inc.

(57) ABSTRACT

The invention relates to a process of combatting microorganisms in industrial processes, particularly in the wood processing industry, by adding glucose oxidase and optionally glucose or a source of glucose to the process solution or slurry.

8 Claims, No Drawings

PROCESS FOR COMBATING MICROORGANISMS

This is a Continuation of application Ser. No. 07/852,129 filed Jun. 15, 1992 now abandoned.

The invention relates to a process of combatting micro-organisms in industrial processes, particularly in the processes of the wood processing industry. The invention is particularly suitable for the treatment of process waters and slurries in the wood processing industry, such as pulp and circulating waters, pigment slurries (kaolin, gypsum and talc slurries, etc.) and pulp and surface sizing slurries (starch slurries, etc.).

Industrial process waters and slurries often contain micro-organisms which may hamper the process and impair the quality of the product. For this reason, it is usually necessary to add chemical biocides to process waters and slurries, such as widespectrum bactericides and fungicides, see e.g. Finnish Patents 76 237 and 75 973 and U.S. Pat. Nos. 3,929,561 and 4,295,932. These biocides are highly poisonous (second-class poisons) and may degrade very slowly in the environment.

It has also been suggested to use enzymes which degrade micro-organisms, see e.g. Finnish Patent 75 973. Enzymes are not poisonous and do not pollute the environment; in addition, they are needed in very small quantities only (a few ppm). The suggested enzymes, however, are hydrolytic enzymes which are specific for certain polysaccharides only, in addition to which bacteria present in process waters usually adapt very rapidly to these enzymes. In other words, these enzymes have a low efficiency, and cannot be used in industrial processes.

In the paper industry in particular, it is absolutely necessary to combat micro-organisms. Pigment slurries and starch solutions often contain plenty of bacteria and fungi, and the process circulating waters contain plenty of nutrients. Furthermore, the temperature and pH are usually favourable, especially for the growth of fungi. Because of their thread-like growth, fungi may cause serious process disturbances, such as blocking of filters, occurrence of pinholes in paper, and colour defects.

Bacteria may cause formation of bad-smelling and even dangerous gases and corrosion of pipe systems and equipment. Only very low bacteria counts are acceptable in food-grade paper products, and the products must not contain any pathogenic bacteria.

By means of the process of the invention, it is possible to combat micro-organisms effectively and economically in industrial processes. The process of the invention uses glucose oxidase which is an oxidation-reduction enzyme (oxidoreductase). The enzyme binds oxygen and produces long-acting hydrogenperoxide which kills substantially all micro-organisms.

EXAMPLE 1

Combatting micro-organisms occurring in a starch or starch derivative slurry to be used in surface sizing Raisamyl 145 starch slurries (100 ml) containing conventional micro-organisms were introduced into 250 ml shaking bottles, and 0–500 U/l glucose oxidase and 0–2 g glucose were added. The mixtures were shaken for several days at 37° C. The compositions of the sample mixtures and the results obtained are shown in Table I.

EXAMPLE 2

Combatting micro-organisms occurring in a starch or starch derivative slurry to be used in surface sizing AVEBE PERF PW MRR-176 starch slurries (100 ml) containing conventional micro-organisms were introduced into 250 ml shaking bottles, and 50 U/l glucose oxidase, 0–0.9 g glucose and 0.5 g/l trypton yeast extract as a source of nitrogen for the micro-organisms were added. The sample mixtures were shaken for several days at 37° C. The compositions of the sample mixtures and the results obtained are shown in Table II.

EXAMPLE 3

Combatting micro-organisms occurring in circulating waters of pulping process

Circulating water samples (100 ml) containing bacteria of the Bacillus species were introduced into 250 ml shaking bottles, and 0–300 U/l glucose oxidase and 1.5–3 g glucose were added. The sample mixtures were shaken for several hours at 25 to 50° C. The compositions of the sample mixtures and the results obtained are shown in Tables III and IV.

EXAMPLE 4

Combatting micro-organisms occurring in a kaolin slurry

Kaolin slurries (SPS) (100 ml) containing conventional micro-organisms were introduced into 250 ml shaking bottles and 0–1,000 U/l glucose oxidase, 0–2 g glucose, and 2.0 g/l trypton yeast extract as a source of nitrogen for the micro-organism were added. The sample mixtures were shaken for several days at 37° C. Control tests were carried out in which hydrogen peroxide or a microbicide was used in place of glucose oxidase. The compositions of the sample mixtures and the results obtained are shown in Table V.

EXAMPLE 5

Combatting micro-organisms occurring in a kaolin slurry

Kaolin slurries (SPS) (100 ml) containing conventional micro-organisms were introduced into 250 ml shaking bottles, and 0–500 U/l glucose oxidase and 0–2.0 g glucose were added. The sample mixtures were shaken for several days at 37° C. Control tests were carried out in which hydrogen peroxide or a chemical microbicide was used in place of glucose oxidase. The compositions of the sample mixtures and the results obtained are shown in Table VI.

EXAMPLE 6

Combatting micro-organisms occurring in groundwood

Groundwood slurries (100 ml) containing conventional micro-organisms were introduced into 250 ml shaking bottles and 0–300 U/l glucose oxidase and 0–1.6 g glucose were added. The sample mixtures were shaken for several days at 37° C. The compositions of the sample mixtures and the results obtained are shown in Table VII.

TABLE I

Starch slurry*

| | Additives | | | | | | | |
|---|---|---|---|---|---|---|---|---|
| | Glucose oxidase | Glucose | Microbe count/ml | | | | | |
| Test No. | (U/l) | (g/l) | 0 | 1 | 4 | 7 | 14 | 21 (days) |
| 1 | 50 | 0.9 | $6 \times 10^3$ | <10 | <10 | <10 | <10 | <10 |
| 2 | 100 | 1.2 | $6 \times 10^3$ | <10 | <10 | <10 | <10 | <10 |
| 3 | 250 | 1.5 | $6 \times 10^3$ | <10 | <10 | <10 | <10 | <10 |
| 4 | 500 | 2.0 | $6 \times 10^3$ | <10 | <10 | <10 | <10 | <10 |
| 5** | — | 2.0 | $6 \times 10^3$ | $2 \times 10^7$ | $1.7 \times 10^7$ | $1.9 \times 10^7$ | $3 \times 10^7$ | $5.4 \times 10^7$ |
| 6*** | — | — | $6 \times 10^3$ | $1.2 \times 10^8$ | $2.1 \times 10^7$ | $1.5 \times 10^8$ | $4.3 \times 10^7$ | $4.3 \times 10^7$ |

*Cationized starch slurry (Raisamyl 145), dry matter content about 20%, pH 6.2, contains the microbe flora formed during the production and storage of slurry
**Sugar control
***Control

TABLE II

Starch slurry*

| | Additives | | | | | |
|---|---|---|---|---|---|---|
| | Glucose oxidase | Glucose | Microbe count/ml | | | |
| Test No. | (U/l) | (g/l) | 0 | 1 | 3 | 14 (days) |
| 1 | 50 | 0.0 | $2 \times 10^2$ | $4 \times 10^2$ | $1.5 \times 10^2$ | $1.7 \times 10^7$ |
| 2 | 50 | 0.3 | $2 \times 10^2$ | <10 | <10 | 20 |
| 3 | 50 | 0.6 | $2 \times 10^2$ | <10 | <10 | <10 |
| 4 | 50 | 0.9 | $2 \times 10^2$ | <10 | <10 | <10 |
| 5** | — | — | $2 \times 10^2$ | $9.2 \times 10^2$ | $8.6 \times 10^5$ | $1.7 \times 10^7$ |

*Pulp starch slurry (Avebe); dry matter content about 20%; pH 6.7; contains the microbe flora formed during the production and storage of the slurry; trypton yeast extract added 0.5 g/l
**Control

TABLE III

Circulation water*

| | Additives | | | | | |
|---|---|---|---|---|---|---|
| | Glucose oxidase | Glucose | Bacteria count (ng ATP/ml***) | | | |
| Test No. | (U/l) | (g/l) | 0 | 1 | 3 | 6 (h) |
| 1 | 100 | 1.5 | 10 | <10 | <10 | <10 |
| 2 | 300 | 3.0 | 10 | <10 | <10 | <10 |
| 3** | — | 3.0 | 10 | 18 | 28 | 260 |

*Circulation water from a pulp production process; pH 7.0; the sample was sterilized to destroy the natural microbe flora, followed by inoculation by a pure culture of the Bacillus species.
**Sugar control
***Bacterial growth was followed by measuring ATP concentration with an LKB-Wallac luminescence meter.

TABLE IV

Circulation water*

| | Additives | | | Bacteria count (ng ATP/ml***) | | |
|---|---|---|---|---|---|---|
| | Glucose oxidase | Glucose | Hydrogen peroxide | | | |
| Test No. | (U/l) | (g/l) | (ppm) | 0 | 2 | 6 (h) |
| 1 | 100 | 1.5 | — | 8 | 11 | 3 |
| 2 | 300 | 3.0 | — | 8 | 3 | 2 |
| 3** | — | 3.0 | — | 8 | 10 | 80 |
| 4**** | — | — | 30,000 | 8 | 20 | 45 |

*Circulation water from a pulp production process; pH 7.0; the sample was sterilized to destroy natural microbe flora, followed by inoculation by a pure culture of the Bacillus species.
**Sugar control
***Bacterial growth was followed by measuring the ATP concentration with an LKB-Wallac luminescence meter
****Control test (with hydrogen peroxide)

TABLE V

Kaolin slurry*

| | Additives | | | | Bacteria count/ml | | |
|---|---|---|---|---|---|---|---|
| | Glucose oxidase | Glucose | Hydrogen peroxide | Fennosan B-100 | | | |
| Test No. | (U/l) | (g/l) | (ppm) | (ppm) | 0 | 1 | 4 (days) |
| 1 | 50 | 0.9 | — | — | $2.5 \times 10^3$ | 54 | 430 |
| 2 | 100 | 1.2 | — | — | $2.5 \times 10^3$ | 37 | 68 |

TABLE V-continued

Kaolin slurry*

| | Additives | | | | | | |
|---|---|---|---|---|---|---|---|
| | Glucose oxidase | Glucose | Hydrogen peroxide | Fennosan B-100 | Bacteria count/ml | | |
| Test No. | (U/l) | (g/l) | (ppm) | (ppm) | 0 | 1 | 4 (days) |
| 3 | 500 | 2.0 | — | — | $2.5 \times 10^3$ | 68 | 63 |
| 4 | 1000 | 3.0 | — | — | $2.5 \times 10^3$ | 93 | 63 |
| 5** | — | — | 250 | — | $2.5 \times 10^3$ | 92 | $5 \times 10^5$ |
| 6** | — | — | 1000 | — | $2.5 \times 10^3$ | 7 | 68 |
| 7*** | — | — | — | 250 | $2.5 \times 10^3$ | $3.2 \times 10^3$ | $1.6 \times 10^6$ |
| 8**** | — | 1.5 | — | — | $2.5 \times 10^3$ | 70 | $5 \times 10^6$ |
| 9***** | — | — | — | — | $2.5 \times 10^3$ | 70 | $10^7$ |

*SPS kaolin slurry (ECC), dry matter content about 50%, pH 7.5; contains the microbe flora formed during the production and storage of the slurry; 0.25% dispersing agent and 2.0 g/l trypton yeast extract added
**Control test (with hydrogen peroxide)
***Control test (Fennosan B-100)
****Sugar control
*****Control

TABLE VI

Kaolin slurry*

| | Additives | | | | | | | |
|---|---|---|---|---|---|---|---|---|
| | Glucose oxidase | Glucose | Hydrogen peroxide | Fennosan B-100 | Bacterial count/ml) | | | |
| Test No. | (U/l) | (g/l) | (ppm) | (ppm) | 0 | 1 | 4 | 7 (days) |
| 1 | 50 | 0.9 | — | — | $10^4$ | 250 | 206 | 320 |
| 2 | 100 | 1.2 | — | — | $10^4$ | 240 | 210 | 150 |
| 3 | 500 | 2.0 | — | — | $10^4$ | 200 | 32 | 250 |
| 4** | — | — | 250 | — | $2 \times 10^4$ | 100 | 120 | $8 \times 10^4$ |
| 5*** | — | — | 1000 | — | $2 \times 10^4$ | 86 | 10 | 80 |
| 6**** | — | — | — | 250 | $2 \times 10^4$ | 1300 | 860 | 150 |
| 7***** | — | 2.0 | — | — | $10^4$ | 740 | $10^5$ | $2.7 \times 10^8$ |
| 8***** | — | — | — | — | $10^4$ | 2000 | $2 \times 10^4$ | $1.5 \times 10^6$ |

*SPS kaolin (ECC), dry matter content about 50%, pH 6.9; 0.25% dispersing agent added; contains the microbe flora formed during the production and 4-day storage (37° C.)
**Control test (with hydrogen peroxide)
***Control test (Fennosan B-100)
****Sugar control
*****Control

TABLE VII

Groundwood slurry*

| | Additives | | | | | |
|---|---|---|---|---|---|---|
| | Glucose oxidase | Glucose | Bacteria count/ml | | | |
| Test No. | (U/l) | (g/l) | 0 | 5 (h) | 1 (day) | 4 (days) |
| 1 | 300 | 0 | $7.9 \times 10^3$ | $3.2 \times 10^3$ | $6.8 \times 10^6$ | $10^8$ |
| 2 | 300 | 1.5 | $7.9 \times 10^3$ | 74 | 74 | 74 |
| 3** | — | 1.6 | $7.9 \times 10^3$ | $1.3 \times 10^4$ | $1.7 \times 10^6$ | $3.7 \times 10^7$ |
| 4*** | — | — | $3.4 \times 10^3$ | $3.2 \times 10^4$ | $10^7$ | $5.0 \times 10^7$ |

*Groundwood pulp; sterilized and inoculated with the microbe flora of unsterilized groundwood.
**Sugar control
***Control

What is claimed is:

1. A process of combatting micro-organisms contained; industrial processes, comprising adding glucose oxidase and optionally glucose or a source of glucose to industrial process waters or slurries.

2. A process according to claim 1, comprising adding glucose oxidase to the process waters or slurries, in an amount of at least 25 U/litre, preferably 50–1000 U/litre.

3. A process according to claims 1 or 2 for combatting micro-organisms occurring in a kaolin slurry, comprising adding 50–1,000 U/litre glucose oxidase and 0.3–3 g/litre glucose to the slurry.

4. A process according to claims 1 or 2 for combatting micro-organisms occurring in a groundwood or pulp slurry, comprising adding 50–1,000 U/litre glucose oxidase and 0.3–3 g/litre glucose to the slurry.

5. A process according to claims 1 or 2 for combatting micro-organisms occurring in a starch solution, comprising adding 25–500 U/litre glucose oxidase and 0–3 g/litre glucose to the slurry.

6. A process according to claims 1 or 2 for combatting micro-organisms occurring in the circulating waters industrial waste, adding 25–500 U/litre glucose oxidase and 0.3–3 g/litre glucose to the circulating waters.

7. A process according to claims 1 or 2, wherein the temperature is between 2 and 60° C., preferably between 10 and 40° C.

8. A process according to claims 1 or 2, wherein the pH is between 2 and 9, preferably between 5 and 8.

* * * * *